United States Patent
Lee (10) Patent No.: US 8,962,301 B2
(45) Date of Patent: Feb. 24, 2015

(54) BIOCHIP AND METHOD FOR MANUFACTURING THE SAME

(75) Inventor: Nae Rym Lee, Cheonan-si (KR)

(73) Assignee: Intellectual Discovery Co., Ltd., Seoul (KR)

( * ) Notice: Subject to any disclaimer, the term of this patent is extended or adjusted under 35 U.S.C. 154(b) by 598 days.

(21) Appl. No.: 13/252,634

(22) Filed: Oct. 4, 2011

(65) Prior Publication Data

US 2012/0094354 A1    Apr. 19, 2012

(30) Foreign Application Priority Data

Oct. 13, 2010  (KR) .................. 10-2010-0099691
Feb. 22, 2011  (KR) .................. 10-2011-0015705

(51) Int. Cl.
*C12M 1/00*    (2006.01)
*G01N 33/543*  (2006.01)
*G01N 33/02*   (2006.01)

(52) U.S. Cl.
CPC .......... *G01N 33/54373* (2013.01); *G01N 33/02* (2013.01); *Y10S 977/702* (2013.01)
USPC ........ 435/283.1; 435/176; 427/201; 427/204; 977/702

(58) Field of Classification Search
None
See application file for complete search history.

(56) References Cited

U.S. PATENT DOCUMENTS

| | | | |
|---|---|---|---|
| 2004/0086649 A1* | 5/2004 | Chiarelli et al. | 427/384 |
| 2005/0048570 A1* | 3/2005 | Weber et al. | 435/7.1 |
| 2006/0189002 A1* | 8/2006 | Ma et al. | 438/1 |
| 2007/0264656 A1* | 11/2007 | Kawamura | 435/6 |
| 2008/0123089 A1* | 5/2008 | Seul et al. | 356/237.5 |

OTHER PUBLICATIONS

Farzana Darain et al., "On-chip detection of myoglobin based on fluorescence", Biosensors and Bioelectronics, pp. 1744-1750, vol. 24, 2008, Elsevier B.V.

* cited by examiner

*Primary Examiner* — Allison Fox
*Assistant Examiner* — Susan E Fernandez
(74) *Attorney, Agent, or Firm* — H.C. Park & Associates, PLC (57) ABSTRACT

A biochip and a method for manufacturing the same are provided. The biochip can increase a surface area on which biomaterials can be immobilized and improve efficiency of reaction. The biochip includes: a substrate; a coating layer formed on the substrate; and a nanoparticle immobilized on the substrate by the coating layer, a material to be bound to a target material being attached on a surface of the nanoparticle.

15 Claims, 7 Drawing Sheets

- TREAT SURFACE OF SUBSTRATE — S01
- TREAT SUBSTRATE WITH SILICA SOL COATING — S02
- TREAT SURFACE OF SUBSTRATE — S03
- ATTACH SILICA NANOPARTICLE TO SILICA SOL COATING LAYER TO ALLOW MATERIAL TO BIND TO TARGET MATERIAL TO BE ATTACHED — S04
- INTRODUCE FUNCTIONAL GROUP ONTO SILICA NANOPARTICLE — S05
- POSITION BIOMATEIRAL ON SILICA NANOPARTICLE — S06

BIOCHIP AND METHOD FOR MANUFACTURING THE SAME

CROSS-REFERENCE TO RELATED APPLICATIONS

This application claims the benefit of priorities of Korean Patent Application No. 10-2010-0099691 filed on Oct. 13, 2010, and Korean Patent Application No. 10-2011-0015705 filed on Feb. 22, 2011, all of which are incorporated by reference in their entirety herein.

BACKGROUND OF THE INVENTION

1. Field of the invention

The present invention relates to a biochip and a method for manufacturing the same, and more particularly to a biochip used in various fields including analysis of gene expression and gene defects, analysis of protein distribution, disease diagnosis, new drug discovery, and the like, by using biochemical reactions between target materials and biomaterials.

2. Related Art

In manufacturing a substrate for a biochip, silicon or quartz glass has been generally used, and metal, inorganic material, or a polymer material also has been gradually used. A manufacturing process of a plastic chip, which is being recently researched, is slightly different from a manufacturing process of a glass chip or a PDMS chip. The manufacturing process of the plastic chip requires a mold, like the manufacturing process of the PDMNS chip. A mold of the plastic chip is formed of a hard material, such as Si, glass, metal, unlike an SU-8 mold. The mold of the plastic chip is formed through a photolithography process, an etching process, and the like. In addition, a hot embossing process, where the manufactured mold of the plastic chip is used to imprint patterns on a thermoplastic substrate, such as PMMA, is performed. The pattern-imprinted thermoplastic substrate and a plastic flat plate are bound to each other, thereby finally completing the plastic chip. The advantages of the hot embossing process are that the manufacturing method is simple and the manufacturing cost is reduced since the patterns are repetitively imprinted by using the mold. However, the plastic chip manufactured by the above method has a problem in view of surface modification, which is necessary for immobilizing biomaterials on a chip surface thereof. In other words, the plastic chip of the prior art immobilizes a slight amount of biomaterial on the chip surface thereof, and thus is unsuitable for use in analyzing low concentration of specimens.

SUMMARY OF THE INVENTION

The present invention provides a biochip capable of increasing a surface area thereof on which biomaterials can be immobilized and improving efficiency of reaction.

The other objects of the present invention are limited to the above-mentioned object, and other objects of the present invention not mentioned would be clearly understood to those skilled in the art by the following description.

In an aspect, a biochip is provided. The biochip includes: a substrate; a coating layer formed on the substrate; and a nanoparticle immobilized on the substrate by the coating layer, a material to be bound to a target material being attached on a surface of the nanoparticle.

The substrate may be formed of at least one of silicon, glass, metal, inorganic material, polymer, and high molecular material.

The substrate may be formed of one or a mixture of two or more selected from the group consisting of poly(dimethylsiloxane) (PDMS), (poly(methyl methacrylate) (PMMA), cyclic olefin copolymer (COC), polycarbonate (PC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinyl chloride (PVC), polyvinylidene fluoride (PVDF), polybutylene terephthalate (PBT), fluorinated ethylene propylene (FEP), and perfluor alkoxyalkane (PFA).

The coating layer may be a silica coating layer.

The silica coating layer may be formed by coating the substrate with silica sol including silica with a diameter of 5 to 50 nm.

The nanoparticle may be a silica nanoparticle.

The nanoparticle may have a diameter of 100 to 800 nm.

The biochip may further include a biomaterial attached on the surface of the nanoparticle to bind to the target material, wherein the biomaterial may be at least one of antibody, enzyme, protein, DNA, RNA, PNA, nucleic acid, and oligopeptide, which are capable of specifically binding to the target material.

In another aspect, a method for manufacturing a biochip is provided. The method for manufacturing a biochip includes: (a) forming a coating layer on a surface of a substrate; and (b) attaching a nanoparticle to the coating layer to allow a material binding to the target material to be attached thereon.

Step (a) may include at least one of a drop-casting method, a dip-coating method, and a method of injecting a sol solution in a channel formed in a predetermined region by using a syringe pump.

The method may further include drying the substrate on which the coating layer is formed, between step (a) and step (b).

Step (b) may be performed by positioning the nanoparticle at a region on which a biomaterial is to be immobilized, using a pipette or an ink-jet printing method.

The coating layer may be a silica coating layer, and step (a) may include coating the substrate with silica sol including silica with a diameter of 5 to 50 nm.

The nanoparticle may be a silica nanoparticle having a diameter of 100 to 800 nm.

After step (b), the method may further include positioning a biomaterial on the nanoparticle.

After step (b), the method may further include introducing functional group, such as amine group, carboxyl group, aldehyde group, maleimide group, epoxy group, thiol group and N-hydroxysuccinimide ester group, so as to immobilize a biomaterial on the substrate by applying reagent such like 3-Aminopropyltriethoxysilane (APTES), glutaraldehyde, sulfo-SMCC (Sulfosuccinimidyl-4-[N-maleimidomethyl] cyclohexane-1-carboxylate)

DESCRIPTION OF EXEMPLARY EMBODIMENTS

Hereinafter, exemplary embodiments of the present invention will be described in detail with reference to the accompanying drawings. However, the present invention is not limited to the exemplary embodiments to be described below but may be implemented in various forms. Therefore, the exemplary embodiments are provided to enable those skilled in the art to thoroughly understand the teaching of the present invention and to completely inform the scope of the present invention. In the drawings, figurations or the like of components may be exaggerated for more clear explanation, and components expressed by the same reference numeral mean the same component.

(1) Materials of Substrate

A cheap plastic polymer may be used in manufacturing a substrate. The plastic polymer may be one selected from the group consisting of poly(dimethylsiloxane) (PDMS), (poly (methyl methacrylate) (PMMA), cyclic olefin copolymer (COC), polycarbonate (PC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinyl chloride (PVC), polyvinylidene fluoride (PVDF), polybutylene terephthalate (PBT), fluorinated ethylene propylene (FEP), and perfluor alkoxyalkane (PFA).

(2) Preparation of Silica Sol Coating Solution

Examples of a reagent used may include tetraethoxysilane (TEOS), dodecyltriethoxysilane (C12TES), anhydrous ethanol, and a hydrochloric solution. A reagent purchased from Sigma-Aldrich Company was used without pretreatment.

In order to prepare a silica colloid (particularly, silica sol) coating solution, first, TEOS (0.036 mol) and C12TES (0.004 mol) were added into 10 ml of anhydrous ethanol, and followed by stirring at 60° C. for 2 hours.

Next, in order to hydrolyze an ethoxy group of TEOS to a hydroxy group, a hydrochloride solution (~38%; 0.008 mol) was slowly added dropwise thereto while stirring for 10 minutes. Finally, a mole ratio of TEOS:C12TES:H2O:ethanol:HCl was 0.9:0.1:4(x):9:0.2. Here, the ratio (x) of water may be changed within a range of 1 to 10 in some cases.

Next, after the flask was sealed, the reaction was carried out at 80° C. for 2 hours, thereby finally completing a silica sol solution. Silica included in the silica sol may have a diameter of approximately 5 to 50 nm, and silica colloid containing silica with a size of 10 to 20 nm was used in the present exemplary embodiment.

(3) Preparation of Silica Nanoparticles

Silica nanoparticles were synthesized by using a water-in-oil method. First, triton x-100 (1.77 g), 1.6 ml of 1-hexanol, and 400 µl of water were added into 7.6 ml of cyclohexane, followed by stirring.

Then, 100 µl of tetraethyl orthosilicate and 60 µl of ammonia water were added thereinto, followed by stirring for 24 hours.

Then, washing was performed with ethanol, acetone, and water, several times, and nanoparticles were separated by using a centrifugal separator.

Then, the separated nanoparticles were dried by using a vacuum oven at 80° C. for 24 hours, thereby completing silica nanoparticles. The silica nanoparticle may have a diameter of approximately 100 to 800 nm, and silica nanoparticles having diameters of about 300 nm were used in the present exemplary embodiment.

(4) Surface Treatment of Substrate

First, the substrate was immersed in acetone, methanol, distilled water, or the like, and then clearly washed by using an ultrasonic wave generator for 5 to 15 minutes. Then, the substrate was subjected to oxygen plasma treatment by using a plasma surface modifier under the power condition of 100 W for 60 seconds (S01 in FIG. 7).

(5) Silica Sol Coating

After the substrate was subjected to surface treatment, a surface of the substrate was treated with silica sol coating by using about 1 wt % of the prepared silica sol solution through a drop-casting method. Whereas, the silica sol coating may be also performed through dip coating, or the coating may be performed by forming a channel in the substrate at a desired portion and then injecting the silica sol solution through a syringe pump (S02 in FIG. 7).

More specifically, the silica sol coating solution prepared by the above-mentioned method was diluted to 1 wt %. Then, 10 µl of the silica sol coating solution was dropped onto an area of 5 nm width and 5 cm length in the substrate of a copolymer consisting of 70% of polystyrene and 30% of PMMA, and followed by drying. It was confirmed that the silica sol coating was well fixed onto the substrate thus manufactured even though it was immersed in ethanol or water for several hours. Meanwhile, the amount of treatment may be varied depending on the area or the position for silica sol coating.

Figure 1:
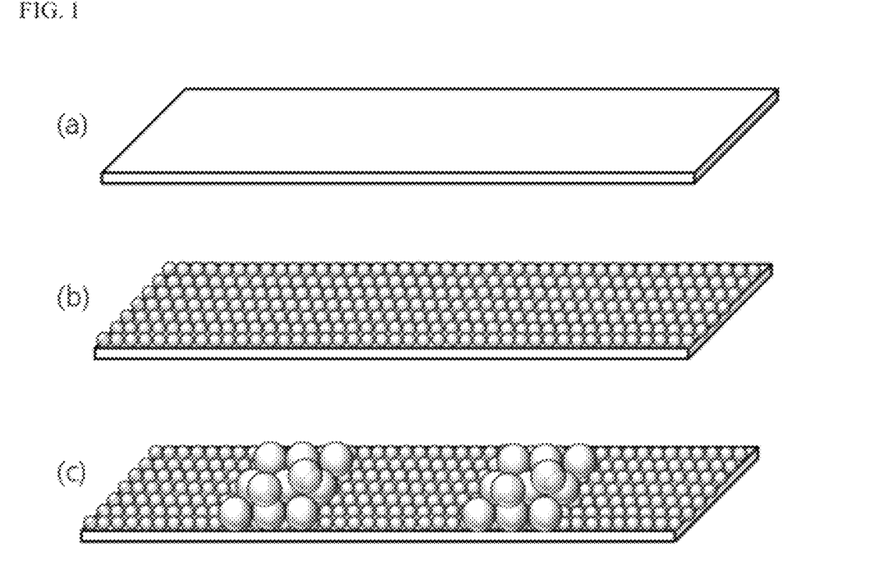
FIG. 1A shows a substrate.
FIG. 1B shows a state in which a surface of a substrate is treated with silica sol coating.
FIG. 1C shows a state in which silica nanoparticles are positioned on a surface of a substrate treated with the silica sol coating.

FIG. 1A shows a substrate, FIG. 1B shows a state in which a surface of a substrate is treated with silica sol coating.

Figure 3:
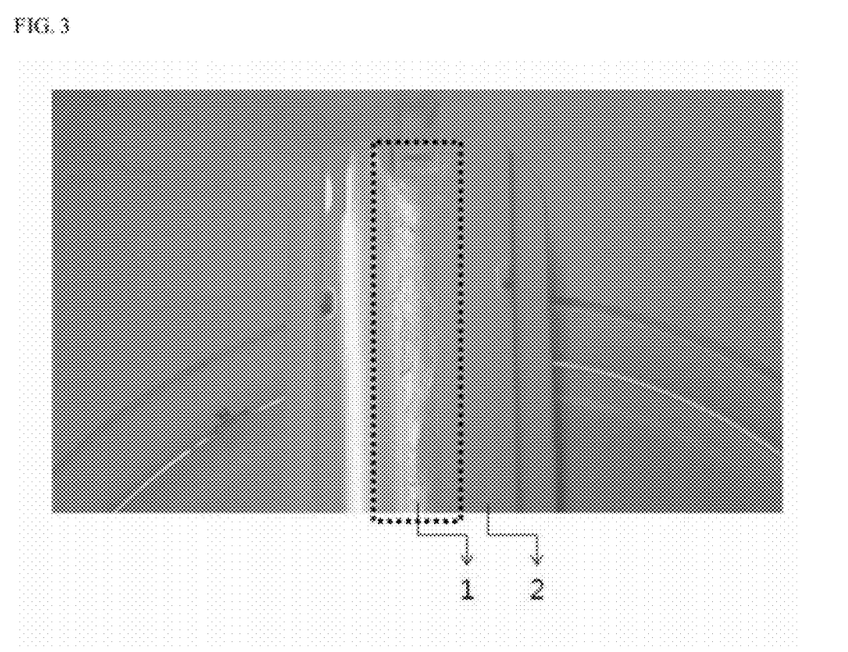
FIG. 3 is a photograph of a surface of a substrate having a silica sol coating-treated part (1) and a silica sol coating-untreated part (2).

FIG. 3 is a photograph of a surface of a substrate having a silica sol coating-treated part (1) and a silica sol coating-untreated part (2).

Figure 4:
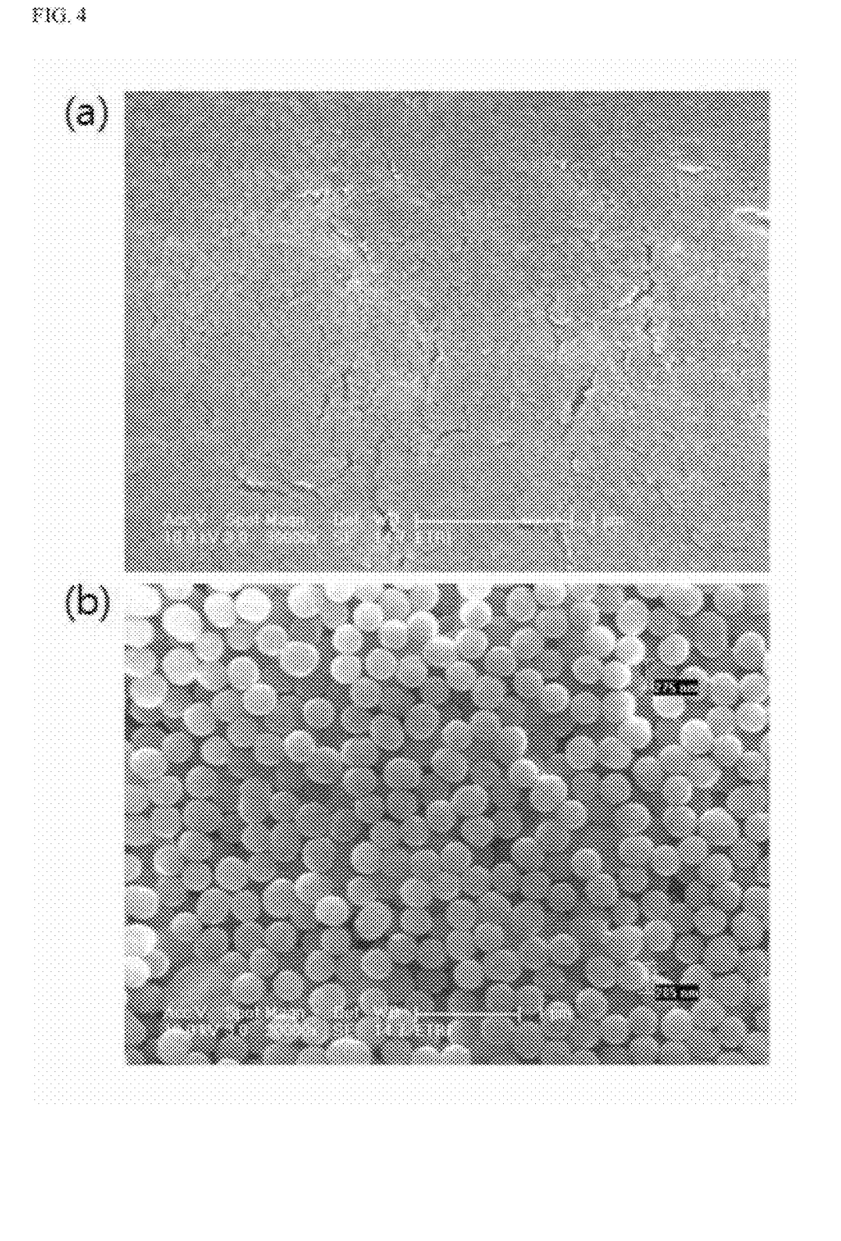
FIG. 4A is a scanning electron microscope (SEM) image of a surface having silica particles of about 10 nm formed by performing silica sol coating.
FIG. 4B is an SEM image of a state in which silica nanoparticles of about 300 nm are positioned on a surface treated with silica sol coating.

FIG. 4A is a scanning electron microscope (SEM) image of a surface having silica particles of about 10 nm formed by performing silica sol coating, and FIG. 4B is an SEM image of a state in which silica nanoparticles of about 300 nm are positioned on a surface treated with silica sol coating.

The coating may be performed by using silica sol, and whereas, the coating may be performed by using another equivalent material capable of increasing hydrophilic property of a hydrophobic surface to suppress a non-specific reaction and facilitating the flow of fluid on the surface.

(6) Surface Treatment of Substrate

After the silica sol coating was completed, the coated substrate was dried by using a vacuum oven at 65° C. for 10 to 15 minutes. Then, the substrate was subjected to plasma treatment (S03 in FIG. 7).

(7) Immobilization of Silica Nanoparticles and Biomaterial

Figure 7:
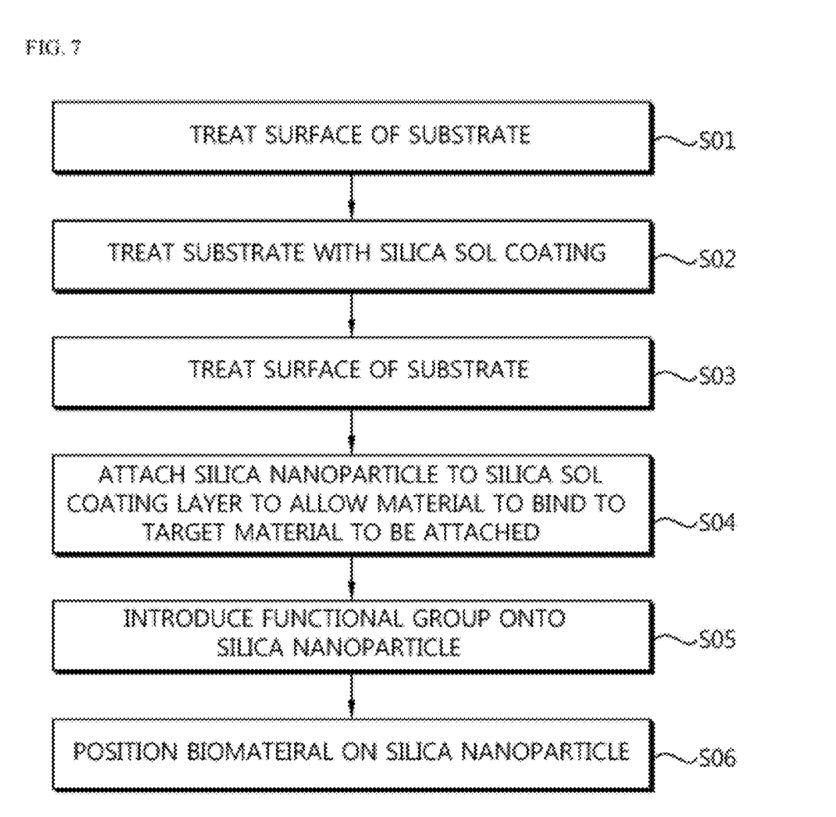
FIG. 7 is a flow chart showing a method for manufacturing a biochip according to an exemplary embodiment of the present invention.

After the surface treatment of the substrate was completed, 5-10 wt % of silica nanoparticles were located on spot portion, at which biomaterials are to be immobilized, with a volume of 0.5 to 1 µl by using a pipette (S04 in FIG. 7).

In another exemplary embodiment, the silica nanoparticles may be positioned by using an ink-jet printing method.

Then, the substrate was dried by using a vacuum oven at 65° C. for 10 to 15 minutes.

FIG. 1C shows a state in which silica nanoparticles are positioned on a surface of a substrate treated with the silica sol coating.

FIG. 2A shows a state in which antibodies are immobilized on a surface of a substrate untreated with silica sol coating, FIG. 2B shows a state in which antibodies are immobilized on a surface of the substrate treated with silica sol coating, and FIG. 2C shows a state in which silica nanoparticles are positioned on a surface of a substrate treated with silica sol coating and then antibodies are immobilized on the surface of the substrate.

Figure 2:
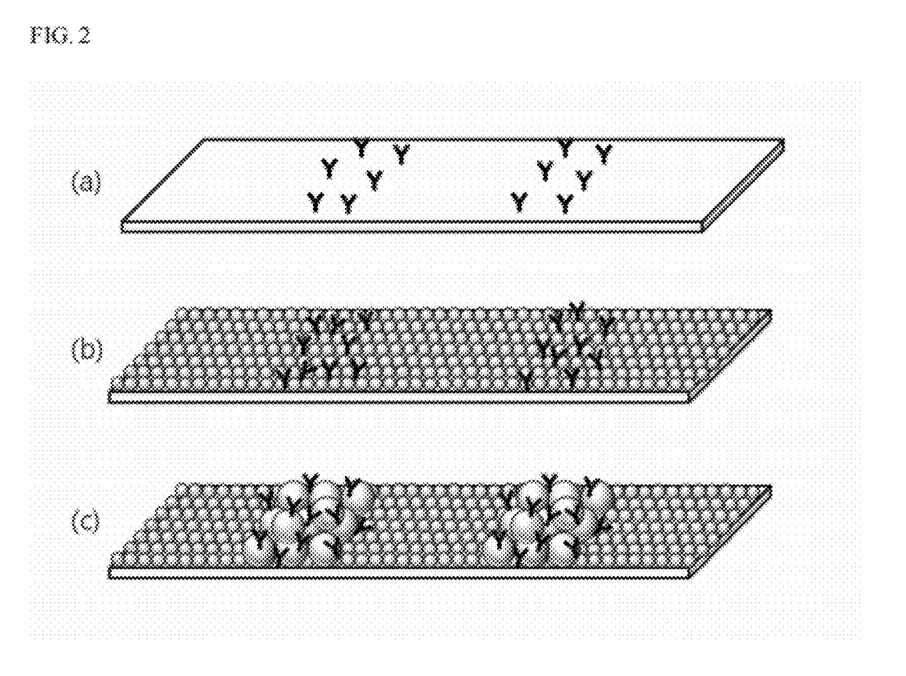
FIG. 2A shows a state in which antibodies are immobilized on a surface of a substrate untreated with silica sol coating.
FIG. 2B shows a state in which antibodies are immobilized on a surface of the substrate treated with silica sol coating.
FIG. 2C shows a state in which silica nanoparticles are positioned on a surface of a substrate treated with silica sol coating and then antibodies are immobilized on the surface of the substrate.

FIG. 2 illustrates that, as a surface area of the substrate widens, the number of immobilized biomaterial (antibody, enzyme, protein, DNA, RNA, PNA, nucleic acid, oligopeptide, or the like) increases.

A functional group may be introduced in order to immobilize the biomaterial onto the spot portion on which the silica nanoparticles are located. (S05 in FIG. 7) In other words, for example, the substrate may be treated with a reagent, such as 3-aminopropyltriethoxysilane (APTES), sulfosuccinimidyl-4-[N-maleimidomethyl]cyclohexane-1-carboxylate (sulfo-SMCC), glutaraldehyde, or the like.

Then, the biomaterial may be located on the spot portion on which silica nanoparticles are positioned (S06 in FIG. 7). The biomaterial, which can be immobilized onto the biochip, is a material specifically bind to a target material, and for example, may include antibody, enzyme, protein, DNA, RNA, PNA, nucleic acid, oligopeptide, and the like.

The silica nanoparticle is preferably used, but a nanoparticle, which consists of other materials functioning to increase the surface area of the biochip or improving the mixing of fluids, may be used.

(8) Detection of Target Material

When the target material is inputted after the biomaterial is immobilized on the spot portion on which silica nanoparticles are located, a biochemical reaction between the biomaterial and the target material occurs. A fluorescent material or a luminescent material may be used to determine whether or not the biochemical reaction occurs. As an example of using the fluorescent material, a residual fluorescent material remaining after a chemical reaction occurring by injecting the target material, which is bound to the fluorescent material, to the biomaterial, is measured by using an external light source. As an example of using the luminescent material, a light emitted from a residual luminescent material remaining after a chemical reaction occurring by injecting the target material, which is bound to the luminescent material, to the biomaterials, is measured.

Figure 5:
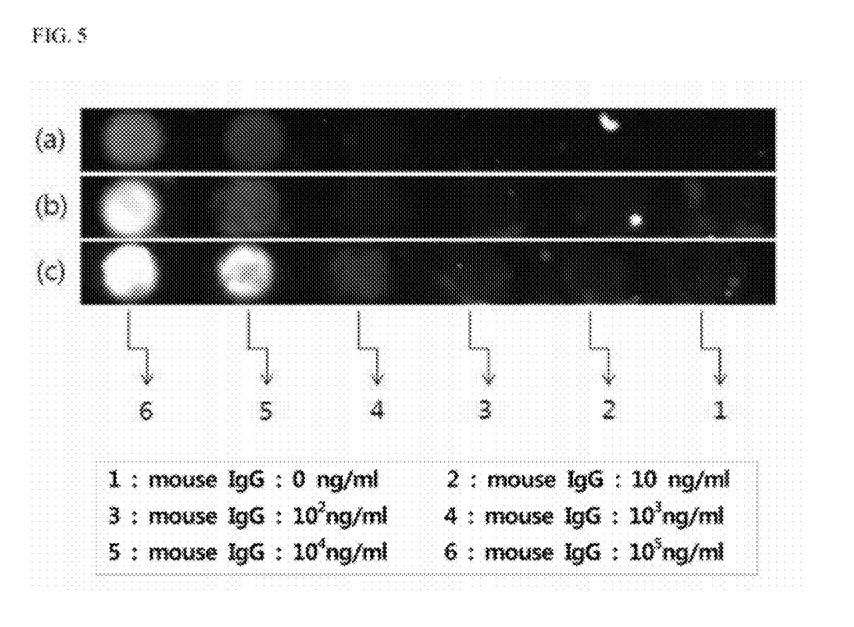
FIG. 5A is a fluorescence image obtained from an experiment using a substrate on which neither silica sol coating nor silica nanoparticle immobilization is performed.
FIG. 5B is a fluorescence image obtained from an experiment using a substrate on which silica sol coating is performed but silica nanoparticle immobilization is not performed.
FIG. 5C shows a fluorescence image obtained from an experiment using a substrate on which both silica sol coating and silica nanoparticle immobilization are performed.

FIG. 5A is a fluorescence image obtained from an experiment using a substrate on which neither silica sol coating nor silica nanoparticle immobilization is performed, FIG. 5B is a fluorescence image obtained from an experiment using a substrate on which silica sol coating is performed but silica nanoparticle immobilization is not performed, and FIG. 5C shows a fluorescence image obtained from an experiment using a substrate on which both silica sol coating and silica nanoparticle immobilization are performed.

Figure 6:
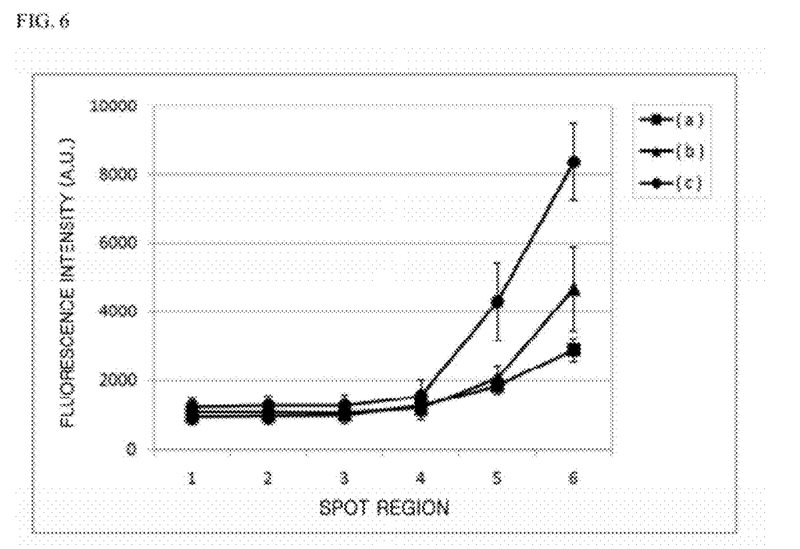
FIG. 6 is a graph showing fluorescence intensities of the fluorescence images obtained from the experiments related to FIGS. 5A to 5C.

FIG. 6 is a graph showing fluorescence intensities of the fluorescence images obtained from the experiments related to FIGS. 5A to 5C.

In the present exemplary embodiment, the substrate made of a polymer of 70% of polystyrene and 30% of PMMA was treated with a reagent, such as 3-aminopropyltriethoxysilane (APTES). Then, glutaraldehyde was injected onto the surface of the substrate treated with APTES in order to introduce a functional group (for example, aldehyde group) capable of immobilizing the biomaterials. Then, mouse IgG was spotted on the surface, on which the glutaraldehyde was injected, at concentrations of 0 ng/ml (Region 1), 10 ng/ml (Region 2), 102 ng/ml (Region 3), 103 ng/ml (Region 4), 104 ng/ml (Region 5), and 105 ng/ml (Region 6), respectively. Then, reaction with high concentration of BSA was performed in order to block activity of the aldehyde group. After that, anti-mouse IgG labeled with Alexa 555, as a fluorescent material, was introduced into the biochip, and then the biochip was photographed by using a fluorescent scanner. The photographed images are shown in FIGS. 5A to 5C. FIG. 6 is a graph showing an average value and an error value of fluorescence intensity obtained by performing the same experiment three times. The fluorescence intensity was measured by using a program, ImageJ, and the relative value of the fluorescence intensity was marked on a vertical axis of the graph.

As shown in these experiment results, the fluorescence intensity was the highest in fluorescence images obtained by experiments using the substrate on which silica sol coating was performed or the surface of the substrate on which silica nanoparticles were immobilized. In other words, it can be confirmed that reaction efficiency was improved by performing silica sol coating and silica nanoparticle immobilization.

The target materials detectable by the biochip according to the present invention are materials capable of specifically binding to the biomaterials. For example, the target material may be antibody, protein, peptide, oligopeptide, nucleic acid, low molecular material, microorganism, fungi, DNA, hydrocarbon, medicinal herbs, or the like.

The biochip according to the present invention may be applied to various apparatuses, which use specific binding between the biomaterials and the target materials. For example, the biochip according to the present invention may be used as a protein chip, a DNA chip, a new drug discovery chip, an environment analysis chip, a toxicity analysis chip, or a food bacteria analysis chip.

According to the exemplary embodiment of the present invention, an area of a surface for immobilizing a biomaterial thereon can be increased. Furthermore, hydrophilic property of a hydrophobic surface can be increased by silica sol coating, thereby facilitating to control flow of fluid on the substrate. Moreover, a mixing effect of the fluid can be improved by using silica nanoparticles.

The present invention is not limited to the above-mentioned effects and other effects, which are not described above, can be obviously understood to those skilled in the art from the claims.

The exemplary embodiment of the present invention, which is described as above and shown in the drawings, should not be interpreted as limiting the technical spirit of the present invention. The scope of the present invention is limited only by matters set forth in the claims and those skilled in the art can modify and change the technical subjects of the present invention in various forms. Therefore, as long as these improvements and changes are apparent to those skilled in the art, they are included in the protective scope of the present invention.

What is claimed is:

1. A biochip, comprising:
   a substrate;
   a silica coating layer disposed on the substrate and comprising silica particles; nanoparticles attached to the substrate by the silica coating layer; and
   a target binding material attached to the nanoparticles,
   wherein the silica coating layer is formed by coating the substrate with silica sol comprising silica particles that each have a diameter of 5 to 50 nm.

2. The biochip of claim 1, wherein the substrate is formed of at least one of silicon, glass, metal, inorganic material, polymer, and high molecular weight material.

3. The biochip of claim 1, wherein the substrate comprises one or more selected from the group consisting of poly(dimethylsiloxane) (PDMS), poly(methyl methacrylate) (PMMA), cyclic olefin copolymer (COC), polycarbonate (PC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinyl chloride (PVC), polyvinylidene fluoride (PVDF), polybutylene terephthalate (PBT), fluorinated ethylene propylene (FEP), and perfluor alkoxyalkane (PFA).

4. The biochip of claim 1, wherein the silica particles are smaller than the nanoparticles.

5. The biochip of claim 1, wherein the nanoparticles comprise silica nanoparticles.

6. The biochip of claim 1, wherein the nanoparticles each have a diameter of 100 to 800 nm.

7. The biochip of claim 1, further comprising a biomaterial specifically bound to the target binding material, wherein the biomaterial is at least one of an antibody, an enzyme, a protein, DNA, RNA, PNA, a nucleic acid, and a oligopeptide.

8. A method for manufacturing a biochip, comprising:
   coating a substrate with a silica sol comprising silica particles that each have a diameter of 5 to 50 nm to form a silica coating layer;
   attaching nanoparticles to the silica coating layer; and
   attaching a target binding material to the nanoparticles.

9. The method of claim 8, wherein the coating of the substrate comprises drop-casting, a dip-coating, and syringe pump injection.

10. The method of claim 8, further comprising drying the silica coating layer before attaching the nanoparticles.

11. The method of claim 8, wherein the attaching of the nanoparticles comprises positioning the nanoparticles using a pipette or an ink-jet printing method.

12. The method of claim 8, wherein the substrate comprises one or more selected from the group consisting of poly(dimethylsiloxane) (PDMS), poly(methyl methacrylate) (PMMA), cyclic olefin copolymer (COC), polycarbonate (PC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinyl chloride (PVC), polyvinylidene fluoride (PVDF), polybutylene terephthalate (PBT), fluorinated ethylene propylene (FEP), and perfluor alkoxyalkane (PFA).

13. The method of claim 8, wherein the nanoparticles comprise silica nanoparticles that each have a diameter of 100 to 800 nm.

14. The method of claim 8, further comprising reacting the target binding material with a biomaterial.

15. The method of claim 14, wherein the biomaterial comprises at least one of an antibody, an enzyme, a protein, DNA, RNA, PNA, a nucleic acid, and an oligopeptide, capable of specifically binding to the target binding material.

* * * * *